(12) United States Patent
Rigonatti et al.

(10) Patent No.: US 6,269,816 B1
(45) Date of Patent: Aug. 7, 2001

(54) BUCCAL PROTECTOR

(75) Inventors: Sergio Rigonatti; Rita de Cassia D'Ottaviano Napole, both of Sao Paulo (BR)

(73) Assignee: Fundacao Faculdade de Medicina, Sau Paulo (BR)

( * ) Notice: Subject to any disclaimer, the term of this patent is extended or adjusted under 35 U.S.C. 154(b) by 0 days.

(21) Appl. No.: 09/174,239

(22) Filed: Oct. 16, 1998

(30) Foreign Application Priority Data

Oct. 17, 1997 (BR) ................................. 7702123 U

(51) Int. Cl.[7] ........................................ A61C 5/14
(52) U.S. Cl. ..................... 128/859; 128/861; 128/862; 128/200.26
(58) Field of Search ..................... 128/848, 859–862, 128/200.26; 433/6; 602/902

(56) References Cited

U.S. PATENT DOCUMENTS

| | | | | |
|---|---|---|---|---|
| 2,614,560 | * | 10/1952 | Lee ........................................ | 128/861 |
| 3,126,002 | * | 3/1964 | Owens ................................... | 128/861 |
| 4,495,945 | * | 1/1985 | Liegner ................................. | 128/862 |
| 4,502,478 | * | 3/1985 | Lifton ................................... | 128/862 |
| 5,533,523 | * | 7/1996 | Bass ...................................... | 128/859 |

* cited by examiner

*Primary Examiner*—Michael A. Brown
(74) *Attorney, Agent, or Firm*—Steinberg & Raskin, P.C.

(57) ABSTRACT

A buccal protector made of a single, solid piece of polyurethane resin extracted from castor oil and having a basic dental arcade shape. The buccal protector may be molded from the polyurethane resin. The polyurethane resin preferably has an average polymer which comprehends A219 (type 2¼). The buccal protector includes an orifice for intubation.

13 Claims, 2 Drawing Sheets

BUCCAL PROTECTOR

FIELD OF THE INVENTION

The present invention relates to a buccal protector for use, e.g., during psychiatric treatment.

BACKGROUND OF THE INVENTION

As known in the art, during psychiatric treatment of illnesses such as high degree depression, schizophrenia or when the patient no longer responds to medication, electroshock is often clinically used. Such an electroshock treatment is known as electroconvulsotherapy (E.C.T.). In order to avoid buccal or dental complications during E.C.T., buccal protectors are inserted into the patient's mouth. However, existing buccal protectors have not demonstrated effective protection against all of the patient's buccal conditions. Such protectors must appropriately direct the smashing power arising during E.C.T. and safely guide the buccal soft tissues to prevent damages commonly associated with E.C.T.

It is already known to use a polyester and polypropylene buccal protector, dental arcade shaped, having an outer rim where the patient's lips are supported. A central portion, where the bite is directed during the E.C.T. operation, is provided with a central orifice for the passage of tubes in the event of an emergency.

A disadvantage of such a commonly used buccal protector is the fact that, despite being made out of plastic, it is rather rigid so that with respect to the patient's bite, it provokes buccal and dental traumas. Also, since it is generally U-shaped, it can be ejected by the patient during an E.C.T. session or it can be displaced towards the buccal cavity during an emergency probing.

OBJECTS AND SUMMARY OF THE INVENTION

It is an object of the present invention to provide a new and improved buccal protector.

It is another object of the present invention to provide a new and improved buccal protector which overcomes the drawbacks of prior art buccal protectors mentioned above.

It is still another object of the present invention to provide new and improved buccal protectors which minimize accidents during E.C.T. sessions.

In order to achieve these objects and others, a buccal protector in accordance with the invention, although having the same general shape as other protectors, i.e., the dental arcade, is manufactured out of a polyurethane resin extracted from castor oil (ricinus comuna), with an ideal density for the patient's cheeks to be displaced outwards the teeth or indented groove where the force of electroshock will be received and thus preventing trauma, safely controlling the soft buccal tissues and cushioning the bite. Furthermore, the buccal protector in accordance with the invention provides a better fitting without any danger of being displaced towards the buccal cavity or ejected from the patient's mouth.

The buccal protector is preferably molded from polyurethane resin having an average polymer which comprehends A219 (type 2¼) to thereby provide the buccal protector with an enhanced resin capacity.

Experimental testing of the use of the buccal protector proved that the buccal protector is very effective as to what concerns accommodation of the muscle flexion which follows a severe closing, allowing the E.C.T. operator to have visualization of soft and hard areas of the buccal cavity and assuring, before the stimulation, buccal protection.

The buccal protector in accordance with the invention allows easy insertion and removal thereof into the patient's mouth and furthermore, includes an aperture in a center region to thereby allow intubation.

The construction of the buccal protector enables it to be sterilizable and it can further be autoclaved.

Further, the buccal protector manufactured in accordance with the invention may be made at a low cost.

BRIEF DESCRIPTION OF THE DRAWINGS

A more complete appreciation of the present invention and many of the attendant advantages thereof will be readily understood by reference to the following detailed description when considered in connection with the accompanying drawings in which.

DETAILED DESCRIPTION OF THE PREFERRED EMBODIMENTS

Figure 3:
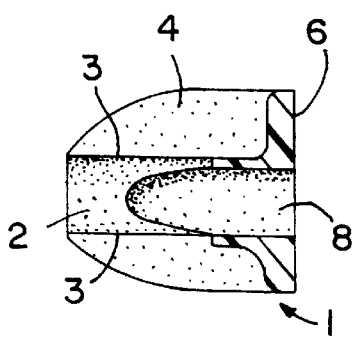
FIG. 3 is a cross-sectional view taken along the line 3—3- of FIG. 2.
Figure 5:
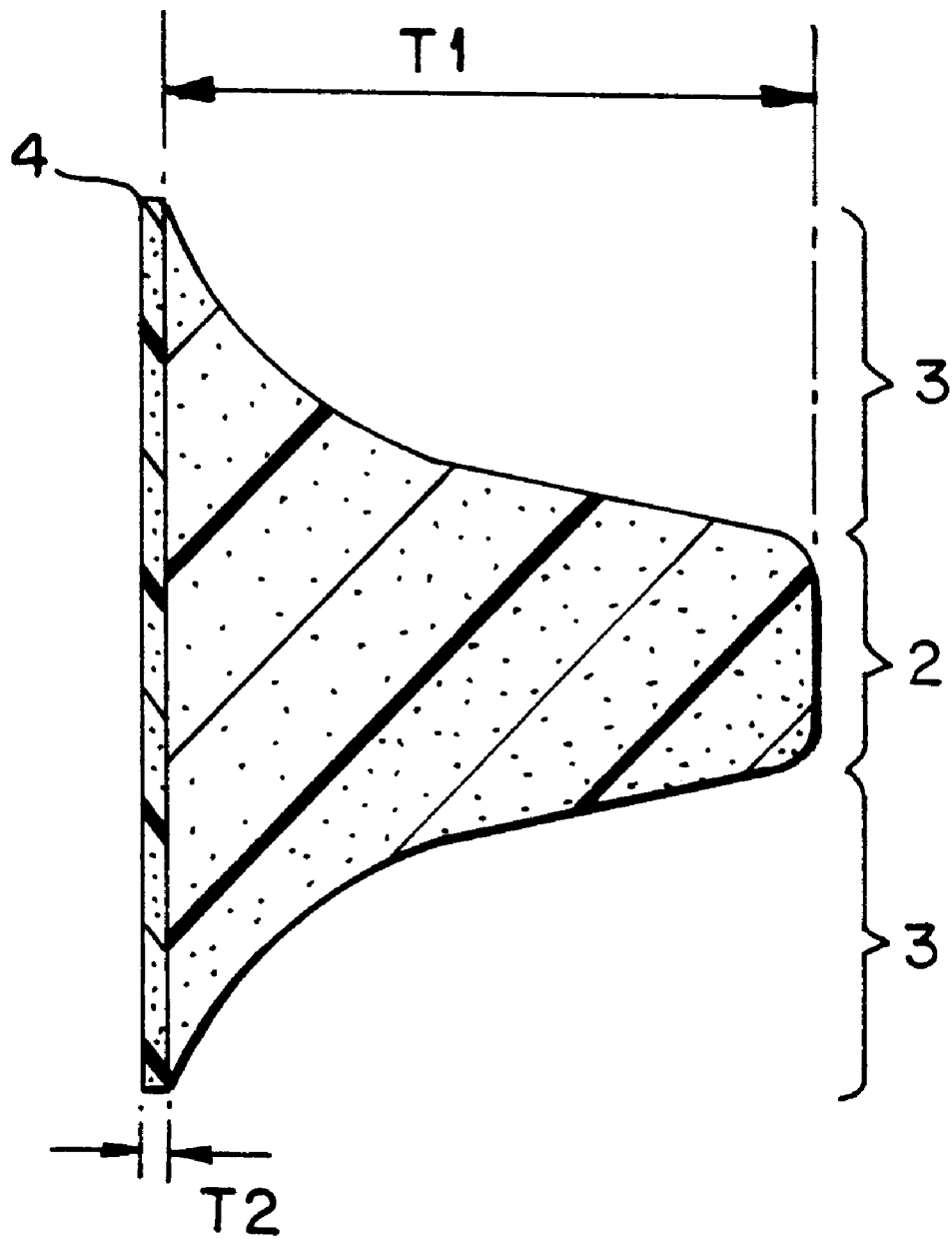
FIG. 5 is a cross-sectional view taken along the line 5—5 of FIG. 2.

Referring to the accompanying drawings wherein like reference characters designate identical or corresponding parts throughout the several views, a buccal protector in accordance with the invention is designated generally at 1 and is a solid piece of material, preferably molded out of a polyurethane resin extracted from castor oil whose average polymer comprehends A219 (type 2¼) which will give it an ideal resin capacity. The buccal protector 1 is formed to have a basic dental arcade shape with a thick arcuate central portion 2 and upper and lower arcuate, sloping portions 3 alongside the central portion 2. The thickness of the upper and lower arcuate portions 3 gradually decreases from a thickness T1 of the central portion 2 to a thickness T2 of an arcuate side edge portion 4 of the buccal protector 1 (see FIG. 5). The edge 4 is laminated and generally conforms to the curvature of the central portion 2, although it is wider than the central portion. The buccal protector 1 is formed so that the central portion 2 is centered relative to the lateral sides of the edge portion 4 (see FIG. 3).

Figure 1:
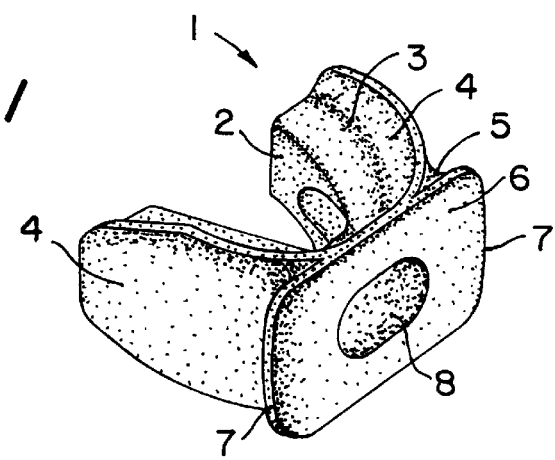
FIG. 1 is a perspective view of the buccal protector in accordance with the invention.
Figure 2:
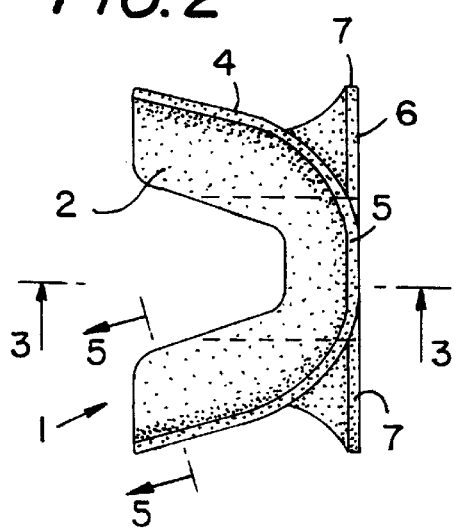
FIG. 2 is an upper view of the buccal protector shown in FIG. 1.

The buccal protector 1 also includes a rounded frontal portion 5 extending outward from the edge portion 4 and on which a pair of projections 6 are formed. Each projection 6 is spaced from a respective opposed portion of the edge portion 4 (FIG. 2). Frontal portion 5 is generally rectangular and extend orthogonally to the central axis of the protector 1. Projections 6 each include a prominent edge 7 which are thus opposed to one another on opposite side of a plane of symmetry of the buccal protector 1. Edges 7 project over the edge portion 4.

Figure 4:
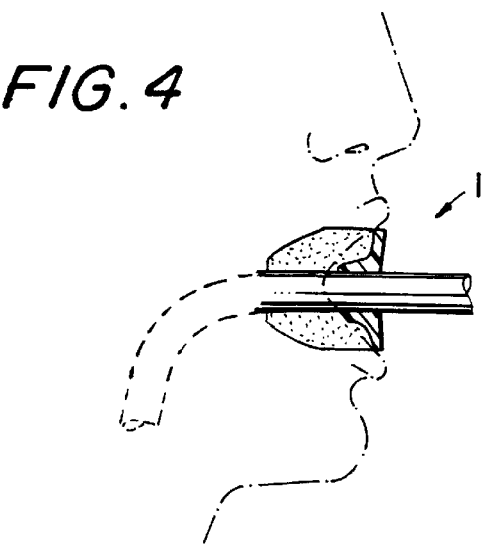
FIG. 4 is an illustration of the application of the buccal protector shown in FIG. 1.

The buccal protector 1 also includes an orifice 8 formed in the central portion 2 for allowing passage of a tube, e.g., during an emergency probing (see FIG. 4).

The examples provided above are not meant to be exclusive. Many other variations of the present invention would be obvious to those skilled in the art, and are contemplated to be within the scope of the appended claims. It is to be understood that although the buccal protector illustrated above is subject to many variations and alterations in shape and dimensions, the present description is not intended to limit the claims to forms and/or dimensions in particular but, rather, to cover all modifications and alterations alternatively, within the objective and scope of the utility model defined by the claims.

What is claimed is:

1. A buccal protector comprising a single, solid piece of polyurethane resin extracted from castor oil, said piece having a basic dental arcade shape and including an arcuate central portion having a first thickness and defining an inner surface of said piece, an arcuate, sloping portion situated alongside each side of said central portion, and an arcuate edge portion having a second thickness smaller than said first thickness and which generally conforms to the curvature of said central portion, said arcuate edge portion defining an outer surface of said piece, said sloping portions each having a thickness decreasing from said first thickness to said second thickness.

2. The buccal protector of claim 1, wherein said edge portion is wider than said central portion.

3. The buccal protector of claim 1, wherein said edge portion is laminated.

4. The buccal protector of claim 1, wherein said sloping portions have a curving slope.

5. The buccal protector of claim 1, wherein said central portion, said sloping portions and said edge portion are arranged such that said central portion is centered between lateral sides of said edge portion.

6. The buccal protector of claim 1, wherein said piece further includes a frontal portion extending outward from said edge portion.

7. The buccal protector of claim 6, wherein said frontal portion has a rounded rear surface conforming to the surface of said edge portion and a planar front surface.

8. The buccal protector of claim 7, wherein said planar front surface is substantially rectangular.

9. The buccal protector of claim 6, wherein said frontal portion includes edges spaced from a respective opposed portion of said edge portion.

10. The buccal protector of claim 1, wherein said central portion includes an orifice.

11. The buccal protector of claim 1, wherein said piece is molded from the polyurethane resin.

12. The buccal protector of claim 1, wherein the polyurethane resin has an average polymer which comprehends A219 (type 2¼).

13. The buccal protector of claim 1, wherein said central portion consists of a single orifice.

* * * * *